United States Patent
Berry

Patent Number: 5,858,010
Date of Patent: Jan. 12, 1999

[54] PERSONAL HYGENIC WASHING SYSTEM

[76] Inventor: Melodye W. Berry, 228 Inner Circle, Maxwell AFB, Ala. 36113

[21] Appl. No.: 764,065

[22] Filed: Nov. 6, 1996

[51] Int. Cl.$^6$ .................................................. A61M 31/00

[52] U.S. Cl. ......................... 604/279; 604/212; 222/575; 222/633; 222/568

[58] Field of Search .................................. 604/19, 27, 37, 604/39, 55, 181, 183, 185, 187, 212, 257, 261, 275, 279, 192; 222/148, 630, 631, 633, 320, 526, 566, 575, 567, 568

[56] References Cited

U.S. PATENT DOCUMENTS

| | | |
|---|---|---|
| 1,740,240 | 12/1929 | Honey . |
| 2,591,371 | 4/1952 | Nimmo . |
| 2,791,218 | 5/1957 | Nimmo . |
| 3,421,510 | 1/1969 | Kettenbach . |
| 3,916,896 | 11/1975 | Ballard ................................... 128/239 |
| 4,057,060 | 11/1977 | Roth ....................................... 128/232 |
| 4,068,663 | 1/1978 | D'Alessandro ......................... 128/232 |
| 4,167,186 | 9/1979 | Pick et al. .............................. 128/232 |
| 4,287,888 | 9/1981 | Schwarz ................................. 128/239 |
| 4,392,492 | 7/1983 | Pick ......................................... 604/82 |
| 4,772,274 | 9/1988 | Lukacs ................................... 604/275 |
| 5,013,297 | 5/1991 | Cattanach ................................ 604/55 |

*Primary Examiner*—Corrine M. McDermott
*Assistant Examiner*—Cris L. Rodriguez

[57] ABSTRACT

A new Personal Hygenic Washing System for douching the external pelvic area as well as for use internally. The inventive device includes a contoured cleaning member having a plurality of irrigation holes, a squeezable bottle and means for attaching the cleaning member to the squeezable bottle.

2 Claims, 3 Drawing Sheets

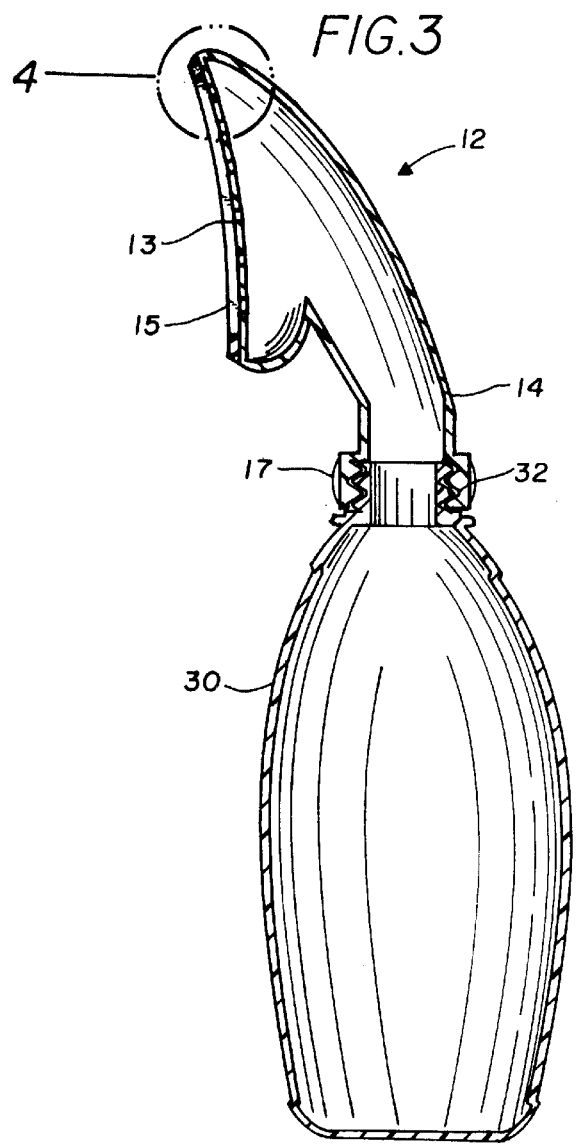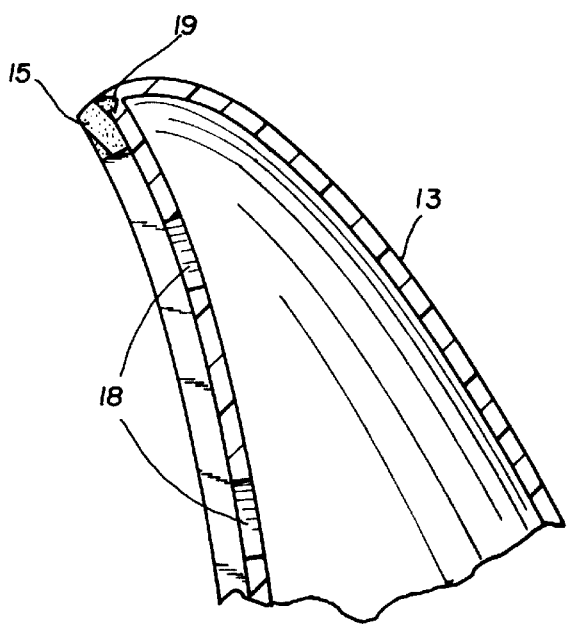

PERSONAL HYGENIC WASHING SYSTEM

BACKGROUND OF THE INVENTION

1. Field of the Invention

The present invention relates to douching devices and more particularly pertains to a new Personal Hygenic Washing System for douching the external pelvic area as well as for use internally.

2. Description of the Prior Art

The use of douching devices is known in the prior art. More specifically, douching devices heretofore devised and utilized are known to consist basically of familiar, expected and obvious structural configurations, notwithstanding the myriad of designs encompassed by the crowded prior art which have been developed for the fulfillment of countless objectives and requirements.

Known prior art douching devices include U.S. Pat. Nos. 5,013,297; 3,916,896; 4,287,888; and 4,405,321.

While these devices fulfill their respective, particular objectives and requirements, the aforementioned patents do not disclose a new Personal Hygenic Washing System. The inventive device includes a contoured cleaning member having a plurality of irrigation holes, a squeezable bottle and means for attaching the cleaning member to the squeezable bottle.

In these respects, the Personal Hygenic Washing System according to the present invention substantially departs from the conventional concepts and designs of the prior art, and in so doing provides an apparatus primarily developed for the purpose of douching the external pelvic area as well as for use internally.

SUMMARY OF THE INVENTION

In view of the foregoing disadvantages inherent in the known types of douching devices now present in the prior art, the present invention provides a new Personal Hygenic Washing System construction wherein the same can be utilized for douching the external pelvic area as well as for use internally.

The general purpose of the present invention, which will be described subsequently in greater detail, is to provide a new Personal Hygenic Washing System apparatus and method which has many of the advantages of the douching devices mentioned heretofore and many novel features that result in a new Personal Hygenic Washing System which is not anticipated, rendered obvious, suggested, or even implied by any of the prior art douching devices, either alone or in any combination thereof.

To attain this, the present invention generally comprises a contoured cleaning member having a plurality of irrigation holes, a squeezable bottle and means for attaching the cleaning member to the squeezable bottle.

There has thus been outlined, rather broadly, the more important features of the invention in order that the detailed description thereof that follows may be better understood, and in order that the present contribution to the art may be better appreciated. There are additional features of the invention that will be described hereinafter and which will form the subject matter of the claims appended hereto.

In this respect, before explaining at least one embodiment of the invention in detail, it is to be understood that the invention is not limited in its application to the details of construction and to the arrangements of the components set forth in the following description or illustrated in the drawings. The invention is capable of other embodiments and of being practiced and carried out in various ways. Also, it is to be understood that the phraseology and terminology employed herein are for the purpose of description and should not be regarded as limiting.

As such, those skilled in the art will appreciate that the conception, upon which this disclosure is based, may readily be utilized as a basis for the designing of other structures, methods and systems for carrying out the several purposes of the present invention. It is important, therefore, that the claims be regarded as including such equivalent constructions insofar as they do not depart from the spirit and scope of the present invention.

Further, the purpose of the foregoing abstract is to enable the U.S. Patent and Trademark Office and the public generally, and especially the scientists, engineers and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

It is therefore an object of the present invention to provide a new Personal Hygenic Washing System apparatus and method which has many of the advantages of the douching devices mentioned heretofore and many novel features that result in a new Personal Hygenic Washing System which is not anticipated, rendered obvious, suggested, or even implied by any of the prior art douching devices, either alone or in any combination thereof.

It is another object of the present invention to provide a new Personal Hygenic Washing System which may be easily and efficiently manufactured and marketed.

It is a further object of the present invention to provide a new Personal Hygenic Washing System which is of a durable and reliable construction.

An even further object of the present invention is to provide a new Personal Hygenic Washing System which is susceptible of a low cost of manufacture with regard to both materials and labor, and which accordingly is then susceptible of low prices of sale to the consuming public, thereby making such Personal Hygenic Washing System economically available to the buying public.

Still yet another object of the present invention is to provide a new Personal Hygenic Washing System which provides in the apparatuses and methods of the prior art some of the advantages thereof, while simultaneously overcoming some of the disadvantages normally associated therewith.

Still another object of the present invention is to provide a new Personal Hygenic Washing System for douching the external pelvic area as well as for use internally.

Yet another object of the present invention is to provide a new Personal Hygenic Washing System which includes a contoured cleaning member having a plurality of irrigation holes, a squeezable bottle and means for attaching the cleaning member to the squeezable bottle.

Still yet another object of the present invention is to provide a new Personal Hygenic Washing System that is portable.

Even still another object of the present invention is to provide a new Personal Hygenic Washing System that contributes to feminine hygiene.

These together with other objects of the invention, along with the various features of novelty which characterize the invention, are pointed out with particularity in the claims annexed to and forming a part of this disclosure. For a better understanding of the invention, its operating advantages and the specific objects attained by its uses, reference should be had to the accompanying drawings and descriptive matter in which there is illustrated preferred embodiments of the invention.

BRIEF DESCRIPTION OF THE DRAWINGS

The invention will be better understood and objects other than those set forth above will become apparent when consideration is given to the following detailed description thereof. Such description makes reference to the annexed drawings wherein:

FIG. 3 is cross section view taken along line 3—3 of FIG. 2.

FIG. 4 is an enlarged and fragmented view of the external cleaning member head of FIG. 3.

DESCRIPTION OF THE PREFERRED EMBODIMENT

Figure 1:
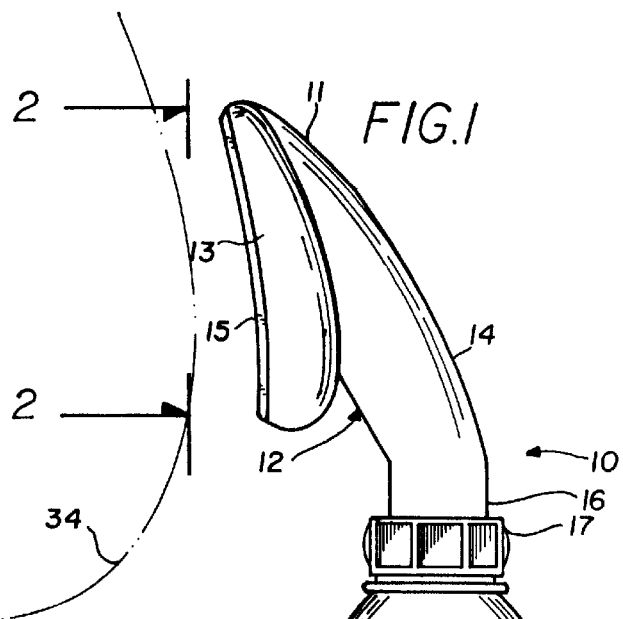
FIG. 1 is a right side plan view of a new Personal Hygenic Washing System according to the present invention.

With reference now to the drawings, and in particular to FIGS. 1 through 6 thereof, a new Personal Hygenic Washing System embodying the principles and concepts of the present invention and generally designated by the reference numeral 10 will be described.

More specifically, it will be noted that the Personal Hygenic Washing System 10 comprises a cleaning member 12 or 20, a squeezable bottle 30 fabricated of a soft rubber and capable of holding two cups of cleaning solution and a means for attaching the cleaning member 12 or 20 to the squeezable bottle 30, the means for attaching the cleaning member 12 or 20 generally comprising a threaded neck 32 and a threaded collar 17 or 26

With reference to FIG. 1, the Personal Hygenic Washing System 10 of the present invention is shown including a squeezable bottle 30 for holding a cleaning solution (not shown), an external cleaning member 12, the external cleaning member 12 being of a hard material such as plastic and comprising a hollow body 14, the hollow body 14 including a hollow body threaded collar 17 disposed at a hollow body inlet end 16 for sealingly and threadingly attaching to the threaded neck 32 (FIG. 3). The hollow body 14 further includes an outlet end 11. A head 13 is disposed at the outlet end 11 and is contoured to conform to the shape of a female pelvic area.

Figure 2:
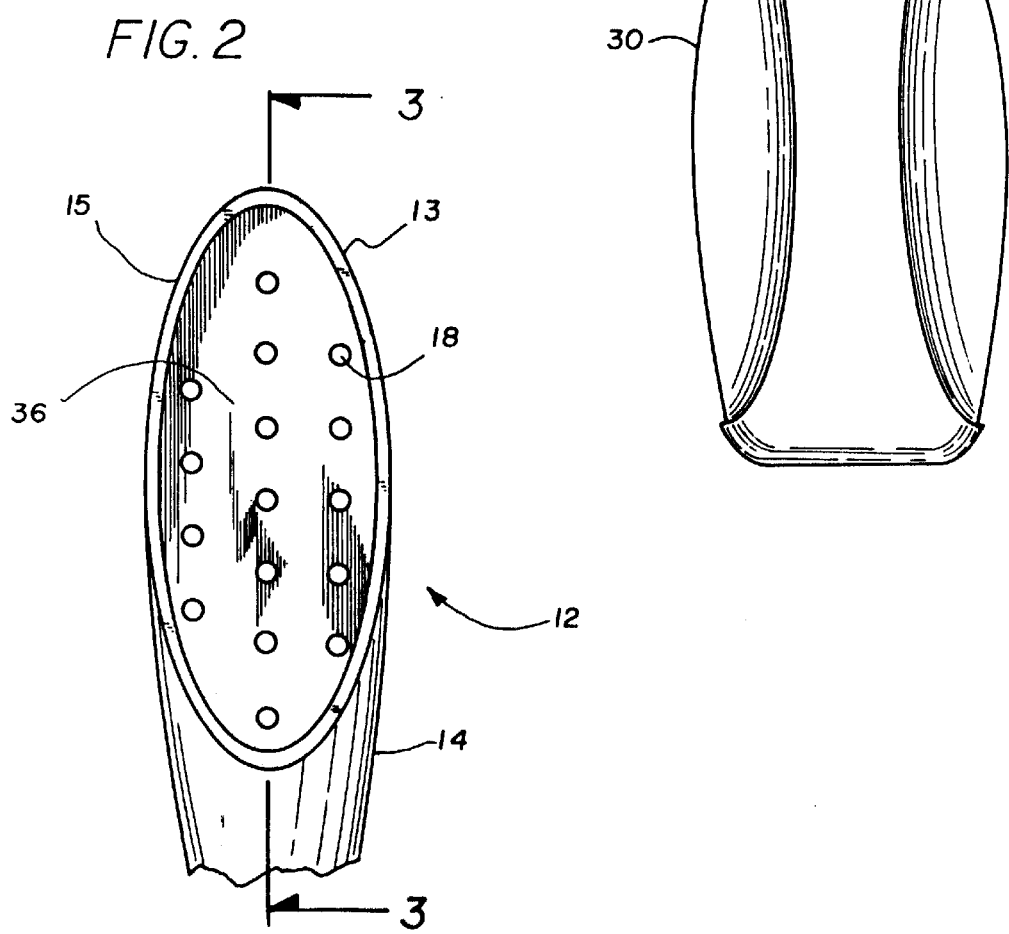
FIG. 2 is a fragmented view thereof showing the external cleaning member head.

With reference to FIG. 2, the head 13 includes a front surface 36 having a plurality of head outlet irrigation holes 18 disposed thereon. A rubber seal 15 is provided for comfort in use and is fixedly attached to an external perimeter of the head 13 by means of retaining means 19, the retaining means 19 comprising a flange embedded in the head external perimeter (FIG. 4).

Figure 5:
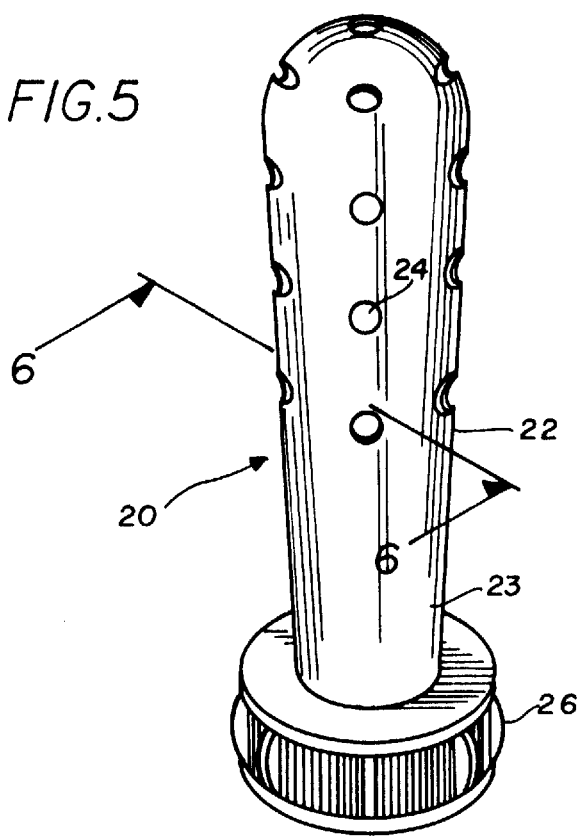
FIG. 5 is a perspective view of the internal cleaning member of the present invention.
Figure 6:
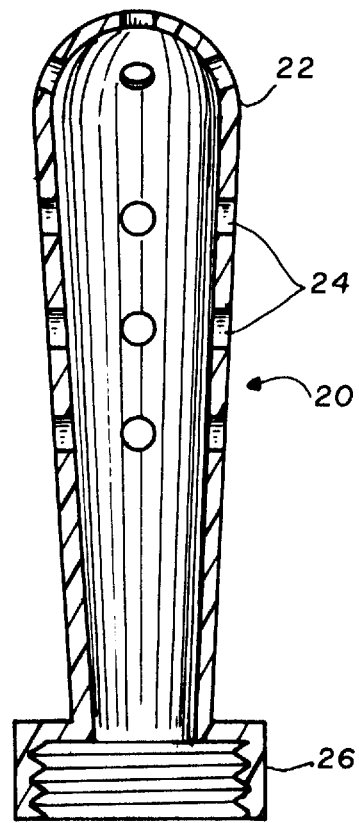
FIG. 6 is a cross sectional view taken along line 6—6 of FIG. 5.

An alternative embodiment of the present invention for use internally is shown in FIGS. 5 and 6. An internal cleaning member 20 is shown including a substantially elongate hollow disposable body 22 adapted to fit inside a vagina. A plurality of internal irrigation holes 24 are provided along the length of the hollow disposable body 22. A hollow disposable body threaded collar 26 is disposed at a hollow disposable body inlet end 23, the hollow disposable body threaded collar 26 being sealingly and threadingly attachable to the threaded neck 32.

For external use the external cleaning member 12 is held in close proximity to the pelvic area 34. A squeezing force is applied to the squeezable bottle 30 forcing the cleaning solution to flow from the squeezable bottle 30 through the hollow body inlet end 16 and out the head outlet irrigation holes 18, whereby the cleaning solution irrigates the pelvic area. For internal use the internal cleaning member 20 is inserted into the vagina and a squeezing force is applied to the squeezable bottle 30 forcing the cleaning solution to flow from the squeezable bottle 30 through the hollow disposable body inlet end 23 and out the internal irrigation holes 24, whereby the cleaning solution irrigates the interior of the vagina.

As to a further discussion of the manner of usage and operation of the present invention, the same should be apparent from the above description. Accordingly, no further discussion relating to the manner of usage and operation will be provided.

With respect to the above description then, it is to be realized that the optimum dimensional relationships for the parts of the invention, to include variations in size, materials, shape, form, function and manner of operation, assembly and use, are deemed readily apparent and obvious to one skilled in the art, and all equivalent relationships to those illustrated in the drawings and described in the specification are intended to be encompassed by the present invention.

Therefore, the foregoing is considered as illustrative only of the principles of the invention. Further, since numerous modifications and changes will readily occur to those skilled in the art, it is not desired to limit the invention to the exact construction and operation shown and described, and accordingly, all suitable modifications and equivalents may be resorted to, falling within the scope of the invention.

What is claimed as being new and desired to be protected by letters patent of the U.S. is as follows:

1. A personal hygenic washing system for douching the pelvic area of a female human body, the washing system comprising:
   a cleaning member;
   a squeezable bottle for holding a cleaning solution;
   a means for attaching the cleaning member to the squeezable bottle; and
   wherein the cleaning member further comprises a hollow body having a head and a hollow body inlet end, the head being positioned at an outlet end of the cleaning member and having a front surface, the front surface of the head having a convex contour to conform to the exterior shape of the female pelvic area to facilitate placement of the head in a snug relationship against the female pelvic area proximate a user's genitalia; and
   the head being structured to include a plurality of head outlet irrigation holes disposed on the front surface of the head;
   wherein the front surface of the head further comprises:
      an external perimeter about the front surface; and
      a seal fixedly attached to the external perimeter for resisting fluid escape from between the front surface and the exterior surface of the female pelvic area during use.

2. A personal hygenic washing system for douching the pelvic area of a female human body, the washing system comprising:

a cleaning member;

a squeezable bottle for holding a cleaning solution;

a means for attaching the cleaning member to the squeezable bottle; and wherein the cleaning member further comprises a hollow body having a head and a hollow body inlet end, the head being positioned at an outlet end of the cleaning member and having a front surface, the front surface of the head having a convex contour to conform to the exterior shape of the female pelvic area to facilitate placement of the head in a snug relationship against the female pelvic area proximate a user's genitalia; and the head being structured to include a plurality of head outlet irrigation holes disposed on the front surface of the head;

wherein the squeezable bottle includes a threaded neck and the means for attaching the cleaning member to the squeezable bottle further comprises:

a hollow body threaded collar, the hollow body threaded collar being disposed at the hollow body inlet end, the hollow body threaded collar being sealingly and threadingly attachable to the threaded neck, whereby the cleaning solution flows from the squeezable bottle through the hollow body inlet end and out the head outlet irrigation holes upon the application of a squeezing force to the squeezable bottle;

wherein the front surface of the head further comprises:

an external perimeter about the front surface; and a seal fixedly attached to the external perimeter for resisting fluid escape from between the front surface and the exterior surface of the female pelvic area during use.

* * * * *